(12) United States Patent
Southan et al.

(10) Patent No.: US 6,180,384 B1
(45) Date of Patent: Jan. 30, 2001

(54) COMPOUNDS

(75) Inventors: Christopher Donald Southan, Stortford; Nicola Anne Burgess, London; Conrad Gerald Chapman, Orpington, all of (GB)

(73) Assignee: SmithKline Beecham plc, Brentford (GB)

( * ) Notice: Under 35 U.S.C. 154(b), the term of this patent shall be extended for 0 days.

(21) Appl. No.: 09/160,494

(22) Filed: Sep. 24, 1998

(30) Foreign Application Priority Data

Feb. 2, 1998 (GB) .................................................. 9802824
Apr. 21, 1998 (GB) .................................................. 9808478

(51) Int. Cl.[7] .............................. C12N 9/48; C07H 21/02; C07K 14/00
(52) U.S. Cl. .......................... 435/212; 536/23.1; 530/350
(58) Field of Search .............................. 536/23.1; 530/350

(56) References Cited

PUBLICATIONS

Wilson et al. "2.2 Mb of contiguous nucleotide sequence from chromosome III of C. elegans", Nature, vol. 368, pp. 32–38 (1994).
Accession #U15182.
Accession #D89276.
Accession #P38821.
Accession #Z98980.
Accession #U13070.

*Primary Examiner*—Ponnathapu Achutamurthy
*Assistant Examiner*—Christian Fronda
(74) *Attorney, Agent, or Firm*—William T. Han; Ratner & Prestia; William T. King

(57) ABSTRACT

METPRO02 polypeptides and polynucleotides and methods for producing such polypeptides by recombinant techniques are disclosed. Also disclosed are methods for utilizing METPRO02 polypeptides and polynucleotides in therapy, and diagnostic assays for such.

31 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1637 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGGGCCGCCT GACCCAAAGC GAAACCGAAA GCCCCGCGGA GGGTGACCTG ACGACTTTCC    60

CGGGACTGGA AGGGGAGTC  CTGTGAGAGA CTAGGTGGCC ATGAACGGTA AGGCCCGCAA   120

AGAGGCGGTG CAGACTGCGG CTAAGGAACT CCTCAAGTTC GTGAACCGGA GTCCCTCTCC   180

TTTCCATGCT GTGGCTGAAT GCCGCAACCG CCTTCTCCAG GCTGGCTTCA GTGAACTCAA   240

GGAGACTGAG AAATGGAATA TTAAGCCCGA GAGCAAGTAC TTCATGACCA GGAACTCCTC   300

CACCATCATA GCTTTTGCTG TAGGGGGCCA GTACGTTCCT GGCAATGGCT TCAGCCTCAT   360

CGGGGCCCAC ACGGACAGCC CCTGCCTCCG GGTGAAACGT CGGTCTCGCC GCAGCCAGGT   420

GGGCTTCCAG CAAGTCGGTG TGGAGACCTA TGGTGGTGGG ATCTGGAGCA CCTGGTTTGA   480

CCGTGACCTG ACTCTGGCTG GACGCGTCAT TGTCAAGTGC CCTACCTCAG GTCGGCTGGA   540

GCAGCAGCTG GTGCACGTGG AGCGGCCCAT TCTTCGCATC CCACACCTGG CCATCCATCT   600

GCAGCGAAAT ATCAACGAGA ACTTTGGGCC CAACACAGAG ATGCATCTAG TCCCCATTCT   660

TGCCACAGCC ATCCAGGAGG AGCTGGAGAA GGGGACTCCT GAGCCAGGGC CTCTCAATGC   720

TGTGGATGAG CGGCACCATT CGGTCCTCAT GTCCCTGCTC TGTGCCCATC TGGGGCTGAG   780

CCCCAAGGAC ATAGTGGAGA TGGAGCTCTG CCTTGCAGAC ACCCAGCCTG CGGTCTTGGG   840

TGGTGCCTAT GATGAGTTCA TCTTTGCTCC TCGGCTGGAC AATCTGCACA GCTGCTTCTG   900

TGCCCTGCAG GCCTTGATAG ATTCCTGTGC AGGCCCTGGC TCCCTGGCCA CAGAGCCTCA   960

CGTGCGCATG GTCACACTCT ATGACAACGA AGAGGTGGGG TCTGAGAGTG CACAGGGAGC  1020

ACAGTCACTG CTGACAGAGC TGGTGCTGCG GCGGATCTCA GCCTCGTGCC AGCACCCGAC  1080

AGCCTTCGAG GAAGCCATAC CCAAGTCCTT CATGATCAGC GCAGACATGG CCCATGCTGT  1140

GCATCCCAAC TACCTGGACA AGCATGAGGA GAACCACCGG CCTTTATTCC ACAAGGGCCC  1200
```

-continued

```
CGTGATCAAG GTGAACAGCA AGCAACGCTA TGCTTCAAAC GCGGTGTCAG AGGCCCTGAT    1260

CCGAGAGGTG GCCAACAAAG TCAAGGTCCC CCTGCAGGAT CTCATGGTCC GGAATGACAC    1320

CCCCTGTGGA ACCACCATTG GACCTATCTT GGCTTCTCGG CTGGGGCTGC GGGTGCTGGA    1380

TTTAGGCAGC CCCCAACTGG CCATGCACTC TATCCGGGAG ATGGCCTGCA CCACAGGAGT    1440

CCTCCAGACC CTCACCCTCT TCAAGGGCTT CTTTGAGCTG TTCCCTTCTC TAAGCCATAA    1500

TCTCTTAGTG GATTGAGCCC TCTTGGAAAG ACTTCTCTGC CATCCCTTTG CACCTGAGAG    1560

GGGAAGTTCT CAGCTGAGCT GAAGCTGGAT TATTAAAGTG GATTGTCACT CAGACTCTAA    1620

GCTCTAAGGG CGAACCA                                                   1637
```

(2) INFORMATION FOR SEQ ID NO:2:

(i) SEQUENCE CHARACTERISTICS:
        (A) LENGTH: 471 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asn Gly Lys Ala Arg Lys Glu Ala Val Gln Thr Ala Ala Lys Glu
  1               5                  10                  15

Leu Leu Lys Phe Val Asn Arg Ser Pro Ser Pro Phe His Ala Val Ala
                 20                  25                  30

Glu Cys Arg Asn Arg Leu Leu Gln Ala Gly Phe Ser Glu Leu Lys Glu
             35                  40                  45

Thr Glu Lys Trp Asn Ile Lys Pro Glu Ser Lys Tyr Phe Met Thr Arg
         50                  55                  60

Asn Ser Ser Thr Ile Ile Ala Phe Ala Val Gly Gly Gln Tyr Val Pro
 65                  70                  75                  80

Gly Asn Gly Phe Ser Leu Ile Gly Ala His Thr Asp Ser Pro Cys Leu
                 85                  90                  95

Arg Val Lys Arg Arg Ser Arg Arg Ser Gln Val Gly Phe Gln Gln Val
            100                 105                 110

Gly Val Glu Thr Tyr Gly Gly Gly Ile Trp Ser Thr Trp Phe Asp Arg
        115                 120                 125

Asp Leu Thr Leu Ala Gly Arg Val Ile Val Lys Cys Pro Thr Ser Gly
    130                 135                 140

Arg Leu Glu Gln Gln Leu Val His Val Glu Arg Pro Ile Leu Arg Ile
145                 150                 155                 160

Pro His Leu Ala Ile His Leu Gln Arg Asn Ile Asn Glu Asn Phe Gly
                165                 170                 175

Pro Asn Thr Glu Met His Leu Val Pro Ile Leu Ala Thr Ala Ile Gln
            180                 185                 190

Glu Glu Leu Glu Lys Gly Thr Pro Glu Pro Gly Pro Leu Asn Ala Val
        195                 200                 205

Asp Glu Arg His His Ser Val Leu Met Ser Leu Leu Cys Ala His Leu
    210                 215                 220

Gly Leu Ser Pro Lys Asp Ile Val Glu Met Glu Leu Cys Leu Ala Asp
225                 230                 235                 240

Thr Gln Pro Ala Val Leu Gly Gly Ala Tyr Asp Glu Phe Ile Phe Ala
                245                 250                 255

Pro Arg Leu Asp Asn Leu His Ser Cys Phe Cys Ala Leu Gln Ala Leu
            260                 265                 270
```

```
Ile Asp Ser Cys Ala Gly Pro Gly Ser Leu Ala Thr Glu Pro His Val
        275                 280                 285
Arg Met Val Thr Leu Tyr Asp Asn Glu Glu Val Gly Ser Glu Ser Ala
    290                 295                 300
Gln Gly Ala Gln Ser Leu Leu Thr Glu Leu Val Leu Arg Arg Ile Ser
305                 310                 315                 320
Ala Ser Cys Gln His Pro Thr Ala Phe Glu Glu Ala Ile Pro Lys Ser
                325                 330                 335
Phe Met Ile Ser Ala Asp Met Ala His Ala Val His Pro Asn Tyr Leu
                340                 345                 350
Asp Lys His Glu Asn His Arg Pro Leu Phe His Lys Gly Pro Val
            355                 360                 365
Ile Lys Val Asn Ser Lys Gln Arg Tyr Ala Ser Asn Ala Val Ser Glu
    370                 375                 380
Ala Leu Ile Arg Glu Val Ala Asn Lys Val Lys Val Pro Leu Gln Asp
385                 390                 395                 400
Leu Met Val Arg Asn Asp Thr Pro Cys Gly Thr Thr Ile Gly Pro Ile
                405                 410                 415
Leu Ala Ser Arg Leu Gly Leu Arg Val Leu Asp Leu Gly Ser Pro Gln
                420                 425                 430
Leu Ala Met His Ser Ile Arg Glu Met Ala Cys Thr Thr Gly Val Leu
            435                 440                 445
Gln Thr Leu Thr Leu Phe Lys Gly Phe Phe Glu Leu Phe Pro Ser Leu
    450                 455                 460
Ser His Asn Leu Leu Val Asp
465                 470
```

(2) INFORMATION FOR SEQ ID NO:3:

(i) SEQUENCE CHARACTERISTICS:
      (A) LENGTH: 2019 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

```
GGTAAGTGGC TCCCGACGGC CCCACTTGAA TTTCGATCCC AGACCGGGTC CGGCGCCCTC      60

CGGNCCANAG CTTTTAGCNNG GTGCTGCAGT GGGGCCGGCCT GACCCAAAGC GAAACCGAAA   120

GCCCCGCGTA GGGTGACCTG ACGACTTTCC CGGGACTGGA AGGGGGAGTC GTGCGACCAC    180

GCGCGGGGCC ATGCAGGTGG CCATGAACGG TAAGGCCCGC AAAGAGGCGG TGCAGACTGC    240

GGCTAAGGAA CTCCTCAAGT TCGTGAACCG GAGTCCCTCT CCTTTCCATG CTGTGGCTGA    300

ATGCCGCAAC CGCCTTCTCC AGGCTGGCTT CAGTGAACTC AAGGAGACTG AGAAATGGAA    360

TATTAAGCCC GAGAGCAAGT ACTTCATGAC CAGGAACTCC TCCACCATCA TAGCTTTTGC    420

TGTAGGGGGC CAGTACGTTC CTGGCAATGG CTTCAGCTCA TCGGGGCCCA CACGGACAGC    480

CCCTGCCTCC GGGTGAAACG TCGGTCTCGC CGCAGCCAGG TGGGCTTCCA GCAAGTCGGT    540

GTGGAGACCT ATGGTGGTGG GATCTGGAGC ACCTGGTTTG ACCGTGACCT TGACTCTGGC    600

TGGACGCGTC ATTGTCAAGT GCCCTACCTC AGGTCGGCTG GAGCAGCAGC TGGTGCACGT    660

GGAGCGGCCC ATTCTTCGCA TCCCACACCT GGCCATCCAT CTGCAGCGAA ATATCAACGA    720

GAACTTTGGG CCCAACACAG AGATGCATCT AGTCCCCATT CTTGCCACAG CCATCCAGGA    780

GGAGCTGGAG AAGGGGACTC CTGAGCCAGG GCCTCTCAAT GCTGTGGATG AGCGGCACCA    840
```

```
TTCGGTCCTC ATGTCCCTGC TCTGTGCCCA TCTGGGGCTG AGCCAAGNGT ACATAGTGGA    900

GATGGAGCTC TGCCTTGCAG ACACCCAGCC TGCGGTCTTG GGTGGTGCCT ATGATGAGTT    960

CATCTTTGCT CCTCGGCTGG ACAATCTGCA CAGCTGCTTC TGTGCCCTGC AGGCCTTGAT   1020

AGATTCCTGT GCAGGCCCTG GCTCCCTGGC CACAGAGCCT CACGTGCGCA TGGTCACACT   1080

CTATGACAAC GAAGAGGTGG GGTCTGAGAG TGCACAGGGA GCACAGTCAC TGCTGACAGA   1140

TGCTGGTGCT GCGGCGGATC TCAGCCTCGT GCCAGCACCC GACAGCCTTC GAGGAAGCCA   1200

TACCCAAGTC CTTCATGATC AGCGCAGACA TGGCCCATGC TGTGATCCCA ACTACCTGGA   1260

CAAGCATGAG GAGAACCACC GGCCTTTATT CCACAAGGGC CCCGTGATCA AGGTGAACAG   1320

CAAGCAACGC TATGCTTCAA ACGCGGTGTC AGAGGCCCTG ATCCGAGAGG TGGCCAACAA   1380

AGTCAAGGTC CCCCTGCAGG ATCTCATGGT CCGGAATGAC ACCCCTGTG GAACCACCAT    1440

TGGACCTATC TTGGCTTCTC GGCTGGGGCT GCGGGTGCTG GATTTAGGCA GCCCCCAACT   1500

GGCCATGCAC TCTATCCGGG AGATGGCCTG CACCACAGGA GTCCTCCAGA CCCTCACCCT   1560

CTTCAAGGGC TTCTTTGAGC TGTTCCCTTC TCTAAGCCAT AATCTCTTAG TGGATTGAGC   1620

CCTCTTGGAA AGACTTCTCT GCCATCCCTT TGCACCTGAG AGGGGAAGTT CTCAGCTGAG   1680

CTGAAGCTGG ATTATTAAAG TGGATTGTCA CTCAGACTCT CCGTGTACGC TTATTTGGAG   1740

ACTAGAGGAG TGGGAGTTGA GCCTGGCTTG AACCTTTGGA ACCAGAAAAG TTGGGGAGCA   1800

GGTGGAGGAG GCCACACTCC TGGGAGCTGA TGGTTTTAAA TCTGGTTTTA AATCTCATCT   1860

CTGTCTCAAG TCCATGTNTG AAGTGGGTGA AGGGTGGACT GGATCCTCAA GCAGAAGGTC   1920

ACTTCTCCCA CCCCTAGTCC TCCACCTGGG AAATGGCCTC AACGGTCTTC CCTCTTTCCA   1980

TCCCCAGAAT GGGTGTCCCG CTCTGCCTTC AGAGATCCT                          2019
```

(2) INFORMATION FOR SEQ ID NO:4:

(i) SEQUENCE CHARACTERISTICS:
        (A) LENGTH: 459 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Val Gln Thr Ala Ala Lys Glu Leu Leu Lys Phe Val Asn Arg Ser Pro
 1               5                  10                  15

Ser Pro Phe His Ala Val Ala Glu Cys Arg Asn Arg Leu Leu Gln Ala
                20                  25                  30

Gly Phe Ser Glu Leu Lys Glu Thr Glu Lys Trp Asn Ile Lys Pro Glu
            35                  40                  45

Ser Lys Tyr Phe Met Thr Arg Asn Ser Ser Thr Ile Ile Ala Phe Ala
        50                  55                  60

Val Gly Gly Gln Tyr Val Pro Gly Asn Gly Phe Ser Ser Ser Gly Pro
65                  70                  75                  80

Thr Arg Thr Ala Pro Ala Ser Gly Xaa Asn Val Gly Leu Ala Ala Ala
                85                  90                  95

Arg Trp Ala Ser Ser Lys Ser Val Trp Arg Pro Met Val Val Gly Ser
                100                 105                 110

Gly Ala Pro Gly Leu Thr Val Thr Leu Thr Leu Ala Gly Arg Val Ile
            115                 120                 125

Val Lys Cys Pro Thr Ser Gly Arg Leu Glu Gln Gln Leu Val His Val
        130                 135                 140
```

```
Glu Arg Pro Ile Leu Arg Ile Pro His Leu Ala Ile His Leu Gln Arg
145                 150                 155                 160

Asn Ile Asn Glu Asn Phe Gly Pro Asn Thr Glu Met His Leu Val Pro
            165                 170                 175

Ile Leu Ala Thr Ala Ile Gln Glu Glu Leu Glu Lys Gly Thr Pro Glu
            180                 185                 190

Pro Gly Pro Leu Asn Ala Val Asp Glu Arg His His Ser Val Leu Met
            195                 200                 205

Ser Leu Leu Cys Ala His Leu Gly Leu Ser Gln Xaa Tyr Ile Val Glu
            210                 215                 220

Met Glu Leu Cys Leu Ala Asp Thr Gln Pro Ala Val Leu Gly Gly Ala
225                 230                 235                 240

Tyr Asp Glu Phe Ile Phe Ala Pro Arg Leu Asp Asn Leu His Ser Cys
                245                 250                 255

Phe Cys Ala Leu Gln Ala Leu Ile Asp Ser Cys Ala Gly Pro Gly Ser
                260                 265                 270

Leu Ala Thr Glu Pro His Val Arg Met Val Thr Leu Tyr Asp Asn Glu
            275                 280                 285

Glu Val Gly Ser Glu Ser Ala Gln Gly Ala Gln Ser Leu Leu Thr Asp
    290                 295                 300

Ala Gly Ala Ala Ala Asp Leu Ser Leu Val Pro Ala Pro Asp Ser Leu
305                 310                 315                 320

Arg Gly Ser His Thr Gln Val Leu His Asp Gln Arg Arg His Gly Pro
                325                 330                 335

Cys Cys Asp Pro Asn Tyr Leu Asp Lys His Glu Glu Asn His Arg Pro
                340                 345                 350

Leu Phe His Lys Gly Pro Val Ile Lys Val Asn Ser Lys Gln Arg Tyr
                355                 360                 365

Ala Ser Asn Ala Val Ser Glu Ala Leu Ile Arg Glu Val Ala Asn Lys
370                 375                 380

Val Lys Val Pro Leu Gln Asp Leu Met Val Arg Asn Asp Thr Pro Cys
385                 390                 395                 400

Gly Thr Thr Ile Gly Pro Ile Leu Ala Ser Arg Leu Gly Leu Arg Val
                405                 410                 415

Leu Asp Leu Gly Ser Pro Gln Leu Ala Met His Ser Ile Arg Glu Met
                420                 425                 430

Ala Cys Thr Thr Gly Val Leu Gln Thr Leu Thr Leu Phe Lys Gly Phe
                435                 440                 445

Phe Glu Leu Phe Pro Ser Leu Ser His Asn Leu
450                 455

(2) INFORMATION FOR SEQ ID NO:5:

(i) SEQUENCE CHARACTERISTICS:
        (A) LENGTH: 1637 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGGCACGATT CGGCAAAACT GGGTGGAGGT CCTCTTGCCC TGGGACTGAA CCTTTGAGCC        60

GAGAGCAGAT CGAGCTAGGA ATCCACATCT GTCGCCAGTG AAGTCCTCGG AGAGCAGAGA      120

TGGCTATGAA CGGCAGGGCT CGGAAAGAGG CCATCCAGGC ATCAGCCCGA GAGCTCCTGA      180
```

```
AGTTCGTGAA CCGGAGTCCC TCTCCTTTCC ACGTCGTGGC TGAGTGCCGC AGCCGCCTCC    240
TCCAGGCTGG CTTCCGTGAA CTCAAGGAAA CAGAGGGCTG GGATATCGTA CCAGAAAACA    300
AGTACTTCTT AACCAGAAAC TCCTCCTCCA TCATTGCTTT TGCTGTGGGG GGCCAGTATG    360
TTCCTGGCAA TGGCTTCAGC CTCATTGGGG CCCACACGGA CAGTCCCTGT CTCAGGGTGA    420
AACGCAAATC GCGCCGAAGC CAGGTGGGCT ACCACCAGGT CGGTGTTGAG ACCTACGGCG    480
GTGGGATCTG GAGCACATGG TTCGACCGGG ACCTGACCTT GGCTGGACGC GTCATTATCA    540
AGTGCCCTAC CTCAGGCCGG CTGGAGCAGA GGCTCGTCCA TATAGAACGG CCCATCCTGC    600
GCATCCCACA TCTGGCCATC CATCTGCAGC GAAATATCAA TGAGAACTTT GGGCCCAACA    660
CAGAGATCCA CCTAGTCCCT ATTCTTGCCA CAGCAGTTCA GGAAGAGCTG GAGAAAGGGA    720
CTCCTGAACC AGGGCCTCTC GGTGCCACTG ATGAGCGGCA CCACTCGGTC CTCATGTCCC    780
TGCTCTGTAC CCATCTGGGC CTGAGTCCTG ACAGCATCAT GGAGATGGAG CTCTGCCTGG    840
CAGACACCCA GCCTGCAGTC CTGGGTGGAG CCTATGAAGA GTTCATCTTC GCTCCTCGAC    900
TGGACAATCT GCACAGCTGC TTCTGTGCCC TGCAGGCATT GATTGATTCC TGTGCATCCC    960
CTGCCTCTCT GGCCAGGGAT CCACATGTGC GCATGGTCAC ACTCTACGAC AATGAAGAGG   1020
TGGGGTCAGA GAGTGCACAA GGAGCACAGT CCCTGCTGAC GGAGCTGATA CTACGGCGCA   1080
TCTCAGCCTC ACCTCAGCGT CTGACTGCCT TCGAGGAAGC CATACCTAAG TCCTTCATGA   1140
TCAGTGCAGA CATGGCCCAT GCTGTGCACC CAAACTACTC GGACAAGCAT GAAGAAAACC   1200
ACCGGCCTTT GTTCCATAAG GGTCCTGTGA TCAAGGTGAA CAGCAAGCAG CGCTACGCCT   1260
CTAATGCAGT GTCTGAGTCC ATGATTCGAG AGGTGGCTGG CCAAGTTGGG GTGCCCCTGC   1320
AGGACCTCAT GGTCAGGAAT GACTCCCCGT GTGGTACCAC CATTGGACCT ATCTTGGCTT   1380
CTCGACTGGG GCTTCGGGTG CTGGACTTAG GCAGCCCCCA ACTGGCTATG CACTCTATCC   1440
GGGAGACAGC CTGTACCACT GGAGTTCTCC AGACCCTCAC CCTTTTCAAG GGCTTCTTTG   1500
AGCTGTTCCC TTCTGTAAGC CGGAACCTCT TAGTGGACTG AGGCCTCTCG CCAAGAGTTG   1560
TCTTCCACCC CTTTGCAATT GAGAGGGGAG GATCTCAGTT TCGCTGATGT TGGATTATTA   1620
AAGTAGATTT TCACTCC                                                   1637
```

(2) INFORMATION FOR SEQ ID NO:6:

(i) SEQUENCE CHARACTERISTICS:
        (A) LENGTH: 471 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Asn Gly Arg Ala Arg Lys Glu Ala Ile Gln Ala Ser Ala Arg Glu
 1               5                  10                  15

Leu Leu Lys Phe Val Asn Arg Ser Pro Ser Pro Phe His Val Val Ala
                20                  25                  30

Glu Cys Arg Ser Arg Leu Leu Gln Ala Gly Phe Arg Glu Leu Lys Glu
            35                  40                  45

Thr Glu Gly Trp Asp Ile Val Pro Glu Asn Lys Tyr Phe Leu Thr Arg
        50                  55                  60

Asn Ser Ser Ile Ile Ala Phe Ala Val Gly Gln Tyr Val Pro
65                  70                  75                  80
```

```
Gly Asn Gly Phe Ser Leu Ile Gly Ala His Thr Asp Ser Pro Cys Leu
                85                  90                  95

Arg Val Lys Arg Lys Ser Arg Ser Gln Val Gly Tyr His Gln Val
            100                 105                 110

Gly Val Glu Thr Tyr Gly Gly Ile Trp Ser Thr Trp Phe Asp Arg
        115                 120                 125

Asp Leu Thr Leu Ala Gly Arg Val Ile Ile Lys Cys Pro Thr Ser Gly
    130                 135                 140

Arg Leu Glu Gln Arg Leu Val His Ile Glu Arg Pro Ile Leu Arg Ile
145                 150                 155                 160

Pro His Leu Ala Ile His Leu Gln Arg Asn Ile Asn Glu Asn Phe Gly
                165                 170                 175

Pro Asn Thr Glu Ile His Leu Val Pro Ile Leu Ala Thr Ala Val Gln
            180                 185                 190

Glu Glu Leu Glu Lys Gly Thr Pro Glu Pro Gly Pro Leu Gly Ala Thr
        195                 200                 205

Asp Glu Arg His His Ser Val Leu Met Ser Leu Leu Cys Thr His Leu
    210                 215                 220

Gly Leu Ser Pro Asp Ser Ile Met Glu Met Glu Leu Cys Leu Ala Asp
225                 230                 235                 240

Thr Gln Pro Ala Val Leu Gly Gly Ala Tyr Glu Glu Phe Ile Phe Ala
                245                 250                 255

Pro Arg Leu Asp Asn Leu His Ser Cys Phe Cys Ala Leu Gln Ala Leu
            260                 265                 270

Ile Asp Ser Cys Ala Ser Pro Ala Ser Leu Ala Arg Asp Pro His Val
        275                 280                 285

Arg Met Val Thr Leu Tyr Asp Asn Glu Glu Val Gly Ser Glu Ser Ala
    290                 295                 300

Gln Gly Ala Gln Ser Leu Leu Thr Glu Leu Ile Leu Arg Arg Ile Ser
305                 310                 315                 320

Ala Ser Pro Gln Arg Leu Thr Ala Phe Glu Glu Ala Ile Pro Lys Ser
                325                 330                 335

Phe Met Ile Ser Ala Asp Met Ala His Ala Val His Pro Asn Tyr Ser
            340                 345                 350

Asp Lys His Glu Glu Asn His Arg Pro Leu Phe His Lys Gly Pro Val
        355                 360                 365

Ile Lys Val Asn Ser Lys Gln Arg Tyr Ala Ser Asn Ala Val Ser Glu
    370                 375                 380

Ser Met Ile Arg Glu Val Ala Gly Gln Val Gly Val Pro Leu Gln Asp
385                 390                 395                 400

Leu Met Val Arg Asn Asp Ser Pro Cys Gly Thr Thr Ile Gly Pro Ile
                405                 410                 415

Leu Ala Ser Arg Leu Gly Leu Arg Val Leu Asp Leu Gly Ser Pro Gln
            420                 425                 430

Leu Ala Met His Ser Ile Arg Glu Thr Ala Cys Thr Thr Gly Val Leu
        435                 440                 445

Gln Thr Leu Thr Leu Phe Lys Gly Phe Phe Glu Leu Phe Pro Ser Val
    450                 455                 460

Ser Arg Asn Leu Leu Val Asp
465                 470
```

COMPOUNDS

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach as a means to identify genes and gene products as therapeutic targets is rapidly superceding earlier approaches based on 'positional cloning'. A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to METPRO02, in particular METPRO02 polypeptides and METPRO02 polynucleotides, recombinant materials and methods for their production. In another aspect, the invention relates to methods for using such polypeptides and polynucleotides, including the treatment of arthritis, respiratory diseases, thrombosis, diabetes, cancer, inflammatory disorders, osteoporosis, cardiovascular disorders, hypertension, stroke, asthma, neurodegenerative diseases such as Alzheimer's, and Parkinson's, depression and other CNS disorders, hereinafter referred to as "the Diseases", amongst others. In a further aspect, the invention relates to methods for identifying agonists and antagonists/inhibitors using the materials provided by the invention, and treating conditions associated with METPRO02 imbalance with the identified compounds. In a still further aspect, the invention relates to diagnostic assays for detecting diseases associated with inappropriate METPRO02 activity or levels.

DESCRIPTION OF THE INVENTION

In a first aspect, the present invention relates to MET-PRO02 polypeptides. Such peptides include isolated polypetides comprising an amino acid sequence which has at least 70% identity, preferably at least 80% identity, more preferably at least 90% identity, yet more preferably at least 95% identity, most preferably at least 97–99% identity, to that of SEQ ID NO:2 or SEQ ID NO:6 over the entire length of SEQ ID NO:2 or SEQ ID NO:6. Such polypeptides include those comprising the amino acid of SEQ ID NO:2 or SEQ ID NO:6.

Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 or SEQ ID NO:6 over the entire length of SEQ ID NO:2 or SEQ ID NO:6. Such polypeptides include the polypeptide of SEQ ID NO:2 or SEQ ID NO:6.

Further peptides of the present invention include isolated polypeptides encoded by a polynucleotide comprising the sequence contained in SEQ ID NO:1 or SEQ ID NO:5.

Polypeptides of the present invention are believed to be members of the aminopeptidase family of polypeptides. They are therefore of interest because designing or screening for selective protease antagonists or agonists can lead to the development of new drugs for a variety of diseases (Seife, C., Science 277, 1602–1603). The functional properties of the METPRO02 polypeptides are hereinafter referred to as "METPRO02 activity" or "METPRO02 polypeptide activity" or "biological activity of METPRO02". Also included amongst these activities are antigenic and immunogenic activities of said METPRO02 polypeptides, in particular the antigenic and immunogenic activities of the polypeptide of SEQ ID NO:2 or SEQ ID NO:6. Preferably, a polypeptide of the present invention exhibits at least one biological activity of METRO02.

The polypeptides of the present invention may be in the form of the "mature" protein or may be a part of a larger protein such as a precursor or fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to MET-PRO02 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2 or SEQ ID NO:6, over the entire length of SEQ ID NO:2 or SEQ ID NO:6. In his regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 or SEQ ID NO:5 encoding the polypeptides of SEQ ID NO:2 or SEQ ID NO:6 respectively.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2 or SEQ ID NO:6, over the entire coding region. In this regard, polynucleotides which have at least 97% identify are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 or SEQ ID NO:5 over the entire length of SEQ ID NO:1 or SEQ ID NO:5. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 or SEQ ID NO:5 as well as the polynucleotides of SEQ ID NO:1 and SEQ ID NO:5.

The invention also provides polynucleotides which are complementary to all the above described polynucleotides.

The polynucleotide sequence of SEQ ID NO:1 is a human sequence encoding the polypeptide of SEQ ID NO:2. The polynucleotide sequence of SEQ ID NO:3 is also a human sequence, and encodes the polypeptide labeled "query" of SEQ ID NO:4. The polynucleotide sequence of SEQ ID NO:5 is a mouse sequence that shows a high degree of homology with the human sequences SEQ NO:1 and SEQ ID NO:3, and encodes the mouse polypeptide of SEQ ID NO:6.

The nucleotide sequences of SEQ ID NO:1 and SEQ ID NO:5 show homology with C. elegans cosmid F01F1/gb U13070 (Wilson et al. Nature 368, 32–38(1994). The nucleotide sequence of SEQ ID NO:1is a human DNA sequence and comprises a polypeptide encoding sequence (nucleotide 101 to 1514) encoding a polypeptide of 471 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The nucleotide sequence of SEQ ID NO:5 is a mouse cDNA sequence and comprises a polypeptide encoding sequence (nucleotide 126 to 1539) encoding a polypeptide of 471 amino acids, the polypeptide of SEQ ID NO:6. The nucleotide sequence encoding the polypeptide of SEQ ID NO:6 may be identical to the polypeptide encoding sequence contained in SEQ ID NO:5 or it may be a sequence other than the one contained in SEQ ID NO:5, which, as a result of the redundancy (degeneracy) of the genetic code, also encodes the polypeptide of SEQ ID NO:5.

The polypeptides of the SEQ ID NO:2 and SEQ ID NO:6 are structurally related to other proteins of the aminopeptidase family, having homology and/or structural similarity with C. elegans cosmid F01F1/gb U13070, a translated portion of which is similar to S. cerevisiae vacuolar aminopeptidase (Wilson et al. Nature 368, 32–38 (1994).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one METPRO02 activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide which:

(a) comprises a nucleotide sequence which has at least 70% identity, preferably at least 80% identity, more preferably at least 90% identity, yet more preferably at least 95% identity, even more preferably at least 97–99% identity to SEQ ID NO:3 over the entire length of SEQ ID NO:3;

(b) has a nucleotide sequence which has at least 70% identity, preferably at least 80% identity, more preferably at least 90% identity, yet more preferably at least 95% identity, even more preferably at least 97–99% identity, to SEQ ID NO:3 over the entire length of SEQ ID NO:3;

(c) the polynucleotide of SEQ ID NO:3; or (d) a nucleotide sequence encoding a polypeptide which has at least 70% identity, preferably at least 80% identity, more preferably at least 90% identity, yet more preferably at least 95% identity, even more preferably at least 97–99% identity, to the amino acid sequence of SEQ ID NO:4, over the entire length of SEQ ID NO:4; as well as the polynucleotide of SEQ ID NO:3.

The present invention further provides for a polypeptide which:

(a) comprises an amino acid sequence which has at least 70% identity, preferably at least 80% identity, more preferably at least 90% identity, yet more preferably at least 95% identity, most preferably at least 97–99% identity, to that of SEQ ID NO:4 over the entire length of SEQ ID NO:4;

(b) has an amino acid sequence which is at least 70% identity, preferably at least 80% identity, more preferably at least 90% identity, yet more preferably at least 95% identity, most preferably at least 97–99% identity, to the amino acid sequence of SEQ ID NO:4 over the entire length of SEQ ID NO:4;

(c) comprises the amino acid of SEQ ID NO:4; and (d) is the polypeptide of SEQ ID NO:4; as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognized by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained, using standard cloning and screening techniques, from a cDNA library derived from mRNA in cells of muscle, placenta brain, using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 or SEQ ID NO:6 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1 or SEQ ID NO:5, may be used as hybridization probes for cDNA and genomic DNA or as primers for a nucleic acid amplification (PCR) reaction, to isolate fill-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 or SEQ ID NO:5. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1, SEQ ID NO:5 or fragments thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1, SEQ ID NO:5 or fragments thereof.

The skilled artisan will appreciate that, in many cases, an isolated cDNA sequence will be incomplete, in that the region coding for the polypeptide is short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Sprig Harbor Laboratory Press, Cold Spring Harbor, N.Y. (1989). Preferred such methods include, for instance, calcium phosphate transfection, DEAE-dextran mediated transfection, transfection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extacellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfite or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

This invention also relates to the use of polynucleotides of the present invention as diagnostic reagents. Detection of a mutated form of the gene characterised by the polynucleotide of SEQ ID NO:1 or SEQ ID NO:5 which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled METPRO02 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In anther embodiment, an array of oligonucleotides probes comprising METPRO02 nucleotide sequence or fragments thereof can be constructed to conduct efficient screening of e.g., genetic mutations. Array technology method are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the METPRO02 gene by methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:
(a) a polynucleotide of the present invention, preferably the nucleotide sequence of SEQ ID NO:1, SEQ ID NO:5 or fragments thereof;
(b) a nucleotide sequence complementary to that of (a);
(c) a polypeptide of the present invention, preferably the polypeptide of SEQ ID NO:2, SEQ ID NO:6 or fragments thereof; or
(d) an antibody to a polypeptide of the present invention, preferably to the polypeptide of SEQ ID NO:2 or SEQ ID NO:6.

It will be appreciated that in any such kit, (a), (b), (c) or (d) may comprise a substantial component. Such a kit will be of use in diagnosing a disease or susceptibility to a disease, particularly arthritis, respiratory diseases, thrombosis, diabetes, cancer, inflammatory disorders, osteoporosis, cardiovascular disorders, hypertension, stroke, asthma, neurodegenerative diseases such as Alzheimer's, and Parkinson's, depression and other CNS disorders, amongst others.

The nucleotide sequences of the present invention are also valuable for chromosome localization. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location the physical position of the sequence on the chromosome can be correlate genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The human gene of the present invention maps to human chromosome 2q33-34.

The nucleotide sequences of the present invention are also valuable for tissue localisation. Such techniques allow the determination of expression patterns of the human METRO02 polypeptides in tissues by detection of the mRNAs that encode them. These techniques include in situ hybridziation techniques and nucleotide amplification techniques, for example PCR. Such techniques are well known in the art. Results from these studies provide an indication of the normal functions of the polypeptides in the organism. In addition, comparative studies of the normal expression pattern of human METRO02 mRNAs with that of mRNAs encoded by a human METRO02 gene provide valuable insights into the role of mutant human METPRO02 polypeptides, or that of inappropriate expression of normal human METRO02 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify cots which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring MET-PRO02 activity in the mixture, and comparing the METRO02 activity of the mixture to a standard. Fusion proteins, such as those made from Fc portion and MET-PRO02 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention; which polypeptide is preferably that of SEQ ID NO:2, or SEQ ID NO:6.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors. It will be further appreciated that this will normally be an iterative process.

In a further act, the present invention provides methods of treating abnormal conditions such as, for instance, arthritis, respiratory diseases, thrombosis, diabetes, cancer, inflammatory disorders, osteoporosis, cardiovascular disorders, hypertension, stroke, asthma, neurodegenerative diseases such as Alzheimer's, and Parkinson's, depression and other CNS disorders, related to either an excess of, or an underexpression of, METPRO02 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the METPRO02 polypeptide.

In still another approach, expression of the gene encoding endogenous METPRO02 polypeptide can be inhibited using expression blocking techniques. Known such techniques involve the use of antisense sequences, either internally generated or externally administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human METPRO02 polypeptide may be prevented by using ribozymes specific to the human METPRO02 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave human METPRO02 mRNAs at selected positions thereby preventing translation of the human METPRO02 mRNAs into functional polypeptide. Ribozymes may be synthesised with a natural ribose phosphate backbone and natural bases, as normally found in RNA molecules. Alternatively the ribosymes may be synthesised with non-natural backbones to provide protection from ribonuclease degradation, for example, 2'-O-methyl RNA, and may contain modified bases.

For treating abnormal conditions related to an underexpression of METPRO02 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of METPRO02 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration on include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formula in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in the GCG and Lasergene software packages. Accordingly, in a further aspect, the present invention provides for a computer readable medium having stored thereon a polynucleotide comprising the sequence of SEQ ID NO:1 or SEQ ID NO:5 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, pgs. 1–12 in Post-translational Covalent Modification of Proteins, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al, *J Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)
   Comparison matrix: BLOSSUM62 from Hentikoff and Hentikoff, Proc. Natl. Acad. Sci. USA. 89:10915–10919 (1992)
   Gap Penalty: 12
   Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)
   Comparison matrix: matches=+10, mismatch=0
   Gap Penalty: 50
   Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of in and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

```
SEQUENCE INFORMATION
SEQ ID NO:1
GGGGCCGCCTGACCCAAAGCGAAACCGAAAGCCCCGCGGAGGGTGACCTGACGACTTTCC

CGGGACTGGAAGGGGGAGTCCTGTGAGAGACTAGGTGGCCATGAACGGTAAGGCCCGCAA

AGAGGCGGTGCAGACTGCGGCTAAGGAACTCCTCAAGTTCGTGAACCGGAGTCCCTCTCC

TTTCCATGCTGTGGCTGAATGCCGCAACCGCCTTCTCCAGGCTGGCTTCAGTGAACTCAA

GGAGACTGAGAAATGGAATATTAAGCCCGAGAGCAAGTACTTCATGACCAGGAACTCCTC

CACCATCATAGCTTTTGCTGTAGGGGGCCAGTACGTTCCTGGCAATGGCTTCAGCCTCAT

CGGGGCCCACACGGACAGCCCCTGCCTCCGGGTGAAACGTCGGTCTCGCCGCAGCCAGGT

GGGCTTCCAGCAAGTCGGTGTGGAGACCTATGGTGGTGGGATCGGAGCACCTGGTTTGA

CCGTGACCTGACTCTGGCTGGACGCGTCATTGTCAAGTGCCCTACCTCAGGTCGGCTGGA

GCAGCAGCTGGTGCACGTGGAGCGGCCCATTCTTCGCATCCCACACCTGGCCATCCATCT
```

-continued

```
GCAGCGAAATATCAACGAGAACTTTGGGCCCAACACAGAGATGCATCTAGTCCCCATTCT
TGCCACAGCCATCCAGGAGGAGCTGGAGAAGGQGACTCCTGAGCCAGGGCCTCTCAATGC
TGTGGATGAGCGGCACCATTCGGTCCTCATGTCCCTGCTCTGTGCCCATCTGGGGCTGAG
CCCCAAGGACATAGTGGAGATGGAGCTCTGCCTTGCAGACACCCAGCCTGCGGTCTTGGG
TGGTGCCTATGATGAGTTCATCTTTGCTCCTCGGCTGGACAATCTGCACAGCTGCTTCTG
TGCCCTGCAGGCCTTGATAGATTCCTGTGCAGGCCCTGGCTCCCTGGCCACAGAGCCTCA
CGTGCGCATGGTCACACTCTATGACAACGAAGAGGTGGGGTCTGAGAGTGCACAGGGAGC
ACAGTCACTGCTGACAGAGCTGGTGCTGCGGCGGATCTCAGCCTCGTGCCAGCACCCGAC
AGCCTTCGAGGAAGCCATACCCAAGTCCTTCATGATCAGCGCAGACATGGCCCATGCTGT
GCATCCCAACTACCTGGACAAGCATGAGGAGAACCACCGGCCTTTATTCCACAAGGGCCC
CGTGATCAAGGTGAACAGCAAGCAACGCTATGCTTCAAACGCGGTGTCAGAGGCCCTGAT
CCGAGAGGTGGCCAACAAAGTCAAGGTCCCCCTGCAGGATCTCATGGTCCGGAATGACAC
CCCCTGTGGAACCACCATTGGACCTATCTTGGCTTCTCGGCTGGGGCTGCGGGTGCTGGA
TTTAGGCAGCCCCCAACTGGCCATGCACTCTATCCGGGAGATGGCCTGCACCACAGGAGT
CCTCCAGACCCTCACCCTCTTCAAGGGCTTCTTTGAGCTGTTCCCTTCTCTAAGCCATAA
TCTCTTAGTGGATTGAGCCCTCTTGGAAAGACTTCTCTGCCATCCCTTTGCACCTGAGAG
GGGAAGTTCTCAGCTGAGCTGAAGCTGGATTATTAAAGTGGATTGTCACTCAGACTCTAA
GCTCTAAGGGCGAACCA
SEQ ID NO:2
MNGKARKEAVQTAAKELLKFVNRSPSPFHAVAECRNRLLQAGFSELKETEKWNIKPESKY
FMTRNSSTIIAFAVGGQYVPGNGFSLIGAHTDSPCLRVKRRSRRSQVGFQQVGVETYGGG
IWSTWFDRDLTLAGRVIVKCPTSGRLEQQLVHVERPILRIPHLAIHLQRNINENFGPNTE
MHLVPILATAIQEELEKGTPEPGPLNAVDERHHSVLMSLLCAHLGLSPKDIVEMELCLAD
TQPAVLGGAYDEFIFAPRLDNLHSCFCALQALIDSCAGPGSLATEPHVRMVTLYDNEEVG
SESAQGAQSLLTELVLRRISASCQHPTAFEEAIPKSFMISADMAHAVHPNYLDKHEENHR
PLFHKGPVIKVNSKQRYASNAVSEALIREVANKVKVPLQDLMVRNDTPCGTTIGPILASR
LGLRVLDLGSPQLAMHSIREMACTTGVLQTLTLFKGFFELFPSLSHNLLVD
SEQ ID NO:3
GGTAAGTGGCTCCCGACGGCCCCACTTGAATTTCGATCCCAGACCGGGTCCGGCGCCCTC
CGGNCCANAGCTTTAGCNNGGTGCTGCAGTGGGGCCGCCTGACCCAAAGCGAAACCGAAA
GCCCCGCGTAGGGTGACCTGACGACTTTCCCGGGACTGGAAGGGGGAGTCGTQCGACCAC
GCGCGGGGCCATGCAGGTGGCCATGAACGGTAAGGCCCGCAAAGAGGCGGTGCAGACTGC
VGGCTAAGGAACTCCTCAAGTTCGTGAACCGGAGTCCCTCTCCTTTCCATGCTGTGGCTGA
ATGCCGCAACCGCCTTCTCCAGGCTGGCTTCAGTGAACTCAAGGAGACTGAGAAArGGAA
TATTAAGCCCGAGAGCAAGTACTTCATGACCAGGAACTCCTCCACCATCATAGCTTTTGC
TGTAGGGGGCCAGTACGTTCCTGGCAATGGCTTCAGCTCATCGGGGCCCACACGGACAGC
CCCTGCCTCCGGGTGAAACGTCGGTCTCGCCGCAGCCAGGTGGGCTTCCAGCAAGTCGGT
GTGGAGACCTATGGTGGTGGGATCTGGAGCACCTGGTTTGACCGTGACCTTGACTCTGGC
TGGACGCGTCATTGTCAAGTGCCCTACCTCAGGTCGGCTGGAGCAGCAGCTGGTGCACGT
GGAGCGGCCCATTCTTCGCATCCCACACCTGGCCATCCATCTGCAGCGAAATATCAACGA
GAACTTTGGGCCCAACACAGAGATGCATCTAGTCCCCATTCTTGCCACAGCCATCCAGGA
```

```
GGAGCTGGAGAAGGGGACTCCTGAGCCAGGGCCTCTCAATGCTGTGGATGAGCGGCACCA

TTCGGTCCTCATGTCCCTGCTCTGTGCCCATCTGGGGCTGAGCCAAGNGTACATAGTGGA

GATGGAGCTCTGCCTTGCAGACACCCAGCCTGCGGTCTTGGGTGGTGCCTATGATGAGTT

CATCTTTGCTCCTCGGCTGGACAATCTGCACAGCTGCTTCTGTGCCCTGCAGGCCTTGAT

AGATTCCTGTGCAGGCCCTGGCTCCCTGGCCACAGAGCCTCACGTGCGCATGGTCACACT

CTATGACAACGAAGAGGTGGGGTCTGAGAGTGCACAGGGAGCACAGTCACTGCTGACAGA

TGCTGGTGCTGCGGCGGATCTCAGCCTCGTGCCAGCACCCGACAGCCTTCGAGGAAGCCA

TACCCAAGTCCTTCATGATCAGCGCAGACATGGCCCATGCTGTGATCCCAACTACCTGGA

CAAGCATGAGGAGAACCACCGGCCTTTATTCCACAAGGGCCCCGTGATCAAGGTGAACAG

CAAGCAACGCTATGCTTCAAACGCGGTGTCAGAGGCCCTGATCCGAGAGGTGGCCAACAA

AGTCAAGGTCCCCCTGCAGGATCTCATGGTCCGGAATGACACCCCCTGTGGAACCACCAT

TGGACCTATCTTGGCTTCTCGGCTGGGCTGCGGGTGCTGGATTTAGGCAGCCCCCAACT

GGCCATGCACTCTATCCGGGAGATGGCCTGCACCACAGGAGTCCTCCAGACCCTCACCCT

CTTCAAGGGCTTCTTTGAGCTGTTCCCTTCTCTAAGCCATAATCTCTTAGTGGATTGAGC

CCTCTTGGAAAGACTTCTCTGCCATCCCTTTGCACCTGAGAGGGGAAGTTCTCAGCTGAG

CTGAAGCTGGATTATTAAAGTGGATTGTCACTCAGACTCTCCGTGTACGCTTATTTGGAG

ACTAGAGGAGTGGGAGTTGAGCCTGGCTTGAACCTTTGGAACCAGAAAAGTTGGGGAGCA

GGTGGAGGAGGCCACACTCCTGGGAGCTGATGGTTTTAAATCTGGTTTTAAATCTCATCT

CTGTCTCAAGTCCATGTNTGAAGTGGGTGAAGGGTGGACTGGATCCTCAAGCAGAAGGTC

ACTTCTCCCACCCCTAGTCCTCCACCTGGGAAATGGCCTCAACGGTCTTCCCTCTTTCCA

TCCCCAGAATGGGTGTCCCGCTCTGCCTTCAGAGATCCT

SEQ ID NO:4
Query:   230 VQTAAKELLKFVNRSPSPFHAVAECRNRLLQAGFSELKETEKWNIKPESKYFMTRNSSTI
409

++ AA+E + ++N++ +PFHA  E ++RLLQAGF+EL E+  W+I+P SKYF+T+N S I
Sbjct:    12 IRKAAQEFINYLNKAVTPFHATQEVKDRLLQAGFTELPESGHWDIQPTSKYFVTKNRSAI
71

Query:   410 IAFAVGGQYVPGNGFSSSGPTRTAPASG*NVGLAAARWASSKS-VWRPMVVGSGAPGLTV
586

+AFAVGG Y PG+GFS        +P     L    + KS +   + V + G+
Sbjct:   72  LAFAVGGSYKPGSGFSIVVGHTDSPC------LRVKPISHQKSDKFLQVGVSTYGGGIWR
125

Query:   587 T-----LTLAGRVIVKCPTSGRLEQQLVHVERPILRIPHLAIHLQRNINENFGPNTEMHL
751

T     L++AG VIVK    +L+ +L+ V++P+L  IP+LAIHL+ +    F PNTE L
Sbjct:   126 TWFDRDLSVAGLVIVK--NGEKLQHKLIDVKKPVLFIPNLAIHLETD-RTTFKPNTETEL
182

Query:   752 VPILATAIQEELEKGT-PEP----GPLNAVDERHHSVLMSLLCAHLGLSQXYIVEMELCL
916

PIL T    +    PE     PN +   HH  + L+    G    IV+++L L
Sbjct:   183 RPILETFAAAGINAPQKPESTGFADPRN-ITNNHHPQFLGLIAKEAGCQPEDIVDLDLYL
241

Query:   917 ADTQPAVLGGAYDEFIFAPRLDNLHSCFCALQALIDSCAGPGSLATEPHVRMVTLYDNEE
1096

DT  A + G  DEFI   RLDN  + +  L++S G  S +P +R+  +DNEE
Sbjct:   242 YDTNKAAIVGMEDEFISGARLDNQVGTYTAISGLLESLTGE-SFKNDPQIRIAACFDNEE
300
```

```
                                  -continued
Query: 1097 VGSESAQGAQSLLTD---AGAAADLSLVPAPDSLRGSHTQVLHDQRRHGPCCDPNYLDKH
1267

VGS+SA GA S   T+      +A S       +++ G    +  DQ  H     PNY  KH
Sbjct:  301 VGSDSAMGASSSFTEFVLRRLSAGGSTTAFEEAI-GKSMLISADQA-HAT--HPNYSAKH
356

Query: 1268 EENHRPLFHKGPVIKVNSKQRYASNAVSEALIREVANKVKVPLQDLMVRNDTPCGTTIGP
1447

EENHRP FH G V+KVN  QRYA+ + + A +++VA + +VPLQ ++VRND+PCG+T+GP
Sbjct:  357 EENHRPAFHGGVVVKVNVNQRYATTSTTHAALKQVAFEAQVPLQVVVVRNDSPCGSTVGP
416

Query: 1448 ILASRLGLRVLDLGSPQLAMHSIREMACTTGVLQTLTLFKGFFELFPSLSHNL 1606
            ILA++LGL+ +D+G PQLAMHSIRE A T+ + Q  TL+  F+E    ++  N+

Sbjct:  417 ILATKLGLQTVDVGCPQLAMHSIREFADTSSIYQATTLYSTFYERLSTVLSNM 469
```

SEQ ID NO:4 refers to the sequence labeled "Query" in the alignment

SEQ ID NO:5 (mouse METPR002)
CGGCACGATTCGGCAAAACTGGGTGGAGGTCCTCTTGCCCTGGGACTGAACCTTTGAGCC

GAGAGCAGATCGAGCTAGGAATCCACATCTGTCGCCAGTGAAGTCCTCGGAGAGCAGAGA

TGGCTATGAACGGCAGGGCTCGGAAAGAGGCCATCCAGGCATCAGCCCGAGAGCTCCTGA

AGTTCGTGAACCGGAGTCCCTCTCCTTTCCACGTCGTGGCTGAGTGCCGCAGCCGCCTCC

TCCAGGCTGGCTTCCGTGAACTCAAGGAAACAGAGGGCTGGGATATCGTACCAGAAAACA

AGTACTTCTTAACCAGAAACTCCTCCTCCATCATTGCTTTTGCTGTGGGGGCCAGTATG

TTCCTGGCAATGGCTTCAGCCTCATTGGGCCCACACGGACAGTCCCTGTCTCAGGGTGA

AACGCAAATCGCGCCGAAGCCAGGTGGGCTACCACCAGGTCGGTGTTGAGACCTACGGCG

GTGGGATCTGGAGCACATGGTTCGACCGGGACCTGACCTTGGCTGGACGCGTCATTATCA

AGTGCCCTACCTCAGGCCGGCTGGAGCAGAGGCTCGTCCATATAGAACGGCCCATCCTGC

GCATCCCACATCTGGCCATCCATCTGCAGCGAAATATCAATGAGAACTTTGGGCCCAACA

CAGAGATCCACCTAGTCCCTATTCTTGCCACAGCAGTTCAGGAAGAGCTGGAGAAAGGGA

CTCCTGAACCAGGGCCTCTCGGTGCCACTGATGAGCGGCACCACTCGGTCCTCATGTCCC

TGCTCTGTACCCATCTGGGCCTGAGTCCTGACAGCATCATGGAGATGGAGCTCTGCCTGG

CAGACACCCAGCCTGCAGTCCTGGGTGGAGCCTATGAAGAGTTCATCTTCGCTCCTCGAC

TGGACAATCTGCACAGCTGCTTCTGTGCCCTGCAGGCATTGATTGATTCCTGTGCATCCC

CTGCCTCTCTGGCCAGGGATCCACATGTGCGCATGGTCACACTCTACGACAATGAAGAGG

TGGGGTCAGAGAGTGCACAAGGAGCACAGTCCCTGCTGACGGAGCTGATACTACGGCGCA

TCTCAGCCTCACCTCAGCGTCTGACTGCCTTCGAGGAAGCCATACCTAAGTCCTTCATGA

TCAGTGCAGACATGGCCCATGCTGTGCACCCAAACTACTCGGACAAGCATGAAGAAAACC

ACCGGCCTTTGTTCCATAAGGGTCCTGTGATCAAGGTGAACAGCAAGCAGCGCTACGCCT

CTAATGCAGTGTCTGAGTCCATGATTCGAGAGGTGGCTGGCCAAGTTGGGGTGCCCCTGC

AGGACCTCATGGTCAGGAATGACTCCCCGTGTGGTACCACCATTGGACCTATCTTGGCTT

CTCGACTGGGGCTTCGGGTGCTGGACTTAGGCAGCCCCCAACTGGCTATGCACTCTATCC

GGGAGACAGCCTGTACCACTGGAGTTCTCCAGACCCTCACCCTTTTCAAGGGCTTCTTTG

AGCTGTTCCCTTCTGTAAGCCGGAACCTCTTAGTGGACTGAGGCCTCTCGCCAAGAGTTG

TCTTCCACCCCTTTGCAATTGAGAGGGGAGGATCTCAGTTTCGCTGATGTTGGATTATTA

AAGTAGATTTTCACTCC

-continued

SEQ ID NO:6 (mouse METPR002 polypeptide)

MNGRARKEAIQASARELLKFVNRSPSPFHVVAECRSRLLQAGFRELKETEGWDIVPENKY

FLTRNSSSIIAFAVGGQYVPGNGFSLIGAHTDSPCLRVKRKSRRSQVGYHQVGVETYGGG

IWSTWFDRDLTLAGRVIIKCPTSGRLEQRLVHIERPILRIPHLAIHLQRNINENFGPNTE

IHLVPILATAVQEELEKGTPEPGPLGATDERHHSVLMSLLCTHLGLSPDSIMEMELCLAD

TQPAVLGGAYEEFIFAPRLDNLHSCFCALQALIDSCASPASLARDPHVRMVTLYDNEEVG

SESAQGAQSLLTELILRRISASPQRLTAFEEAIPKSFMISADMAHAVHPNYSDKHEENHR

PLFHKGPVIKVNSKQRYASNAVSESMIREVAGQVGVPLQDLMVRNDSPCGTTIGPILASR

LGLRVLDLGSPQLAMHSIRETACTTGVLQTLTLFKGFFELFPSVSRNLLVD

---

What is claimed is:

1. An expression system comprising a polynucleotide capable of producing a polypeptide comprising the amino acid sequence of SEQ ID NO:2 or of SEQ ID NO:6 when said expression system is present in a compatible host cell.

2. A process for producing a recombinant host cell comprising transforming or transfecting a cell with the expression system of claim 1 such that the host cell, under appropriate culture conditions, produces a polypeptide comprising
   a) the amino acid sequence of SEQ ID NO:2; or
   b) the amino acid sequence of SEQ ID NO:6.

3. A recombinant host cell produced by the process of claim 2.

4. A membrane of a recombinant host cell of claim 3 expressing a polypeptide comprising
   a) the amino acid sequence of SEQ ID NO:2; or
   b) the amino acid sequence of SEQ ID NO:6.

5. A process for producing a polypeptide comprising culturing a host cell of claim 3 under conditions sufficient for the production of said polypeptide and recovering the polypeptide from the culture.

6. An isolated polynucleotide selected form the group consisting of:
   (a) an isolated polynucleotide comprising the polynucleotide set forth in SEQ ID NO:3;
   (b) the polynucleotide set forth in SEQ ID NO:3; and
   (c) an isolated polynucleotide comprising a nucleotide sequence encoding the polypeptide set forth in SEQ ID NO:4.

7. An isolated polynucleotide comprising a nucleotide sequence encoding a polypeptide that has at least 95% identity to the amino acid sequence of SEQ ID NO:2, over the entire length of SEQ ID NO:2, which may include up to $n_a$ amino acid alterations over the entire length of SEQ ID NO:2, wherein $n_a$ is the maximum number of amino acid alterations, and is calculated by the formula $$n_a \leq x_a - (x_a \cdot y),$$

in which $x_a$ is the total number of amino acids in SEQ ID NO:2, and y has a value of 0.95, wherein any non-integer product of $x_a$ and y is rounded down to the nearest integer prior to subtracting such product from $x_a$.

8. An isolated polynucleotide comprising a nucleotide sequence that has at least 95% identity over its entire length to a nucleotide sequence encoding the polypeptide of SEQ ID NO:2, which may include up to $n_n$ nucleotide alterations over the entire region coding for SEQ ID NO:2, wherein $n_n$ is the maximum number of nucleotide alterations, and is calculated by the formula $$n_n \leq x_n - (x_n \cdot y),$$

in which $x_n$ is the total number of nucleotides encoding for SEQ ID NO:2, and y has a value of 0.95, wherein any non-integer product of $x_n$ and y is rounded down to the nearest integer prior to subtracting such product from $x_n$.

9. An isolated polynucleotide comprising a nucleotide sequence which has at least 95% identity to that of SEQ ID NO:1 over the entire length of SEQ ID NO:1, which may include up to $n_n$ nucleotide alterations over the entire length of SEQ ID NO:1, wherein $n_n$ is the maximum number of nucleotide alterations, and is calculated by the formula $$n_n \leq x_n - (x_n \cdot y),$$

in which $x_n$ is the total number of nucleotides in SEQ ID NO:1, and y has a value of 0.95, wherein any non-integer product of $x_n$ and y is rounded down to the nearest integer prior to subtracting such product from $x_n$.

10. An isolated polynucleotide comprising a nucleotide sequence encoding the polypeptide of SEQ ID NO:2.

11. The isolated polynucleotide of claim 8 which is DNA or RNA.

12. The isolated polynucleotide of claim 9 comprising the polynucleotide sequence set forth in SEQ ID NO:1.

13. The isolated polynucleotide of claim 12 consisting of the polynucleotide sequence of SEQ ID NO:1.

14. An isolated polynucleotide obtainable by screening an appropriate library under stringent hybridization conditions with a labeled probe having the sequence of SEQ ID NO:1, said stringent hybridization conditions comprising overnight incubation of hybridization filters at 42° C. in a solution comprising 50% formamide, 5×SSC, 50 mM sodium phosphate having pH 7.6, 5× Denhardt's solution, 10% dextran sulfate, and 20 micrograms per ml denatured, sheared salmon sperm DNA, followed by washing the filters in 0.1×SSC at 65° C., wherein said polynucleotide encodes a metalloprotease polypeptide.

15. An isolated polynucleotide which is fully complementary to
   (a) a nucleotide sequence encoding a polypeptide that is at least 95% identical to the amino acid sequence of SEQ ID NO:2, over the entire length of SEQ ID NO:2, which may include up to $n_a$ amino acid alterations over the entire length of SEQ ID NO:2, wherein $n_a$ is the maximum number of amino acid alterations, and is calculated by the formula $$n_a \leq x_a - (x_a \cdot y),$$

in which $x_a$ is the total number of amino acids in SEQ ID NO:2, and y has a value of 0.95, wherein any non-integer product of $x_a$ and y is rounded down to the nearest integer prior to subtracting such product from $x_a$;
   (b) a nucleotide sequence that is at least 95% identical to a nucleotide sequence encoding the polypeptide of SEQ ID NO:2, over the entire region encoding for SEQ ID NO:2, which may include up to $n_n$ nucleotide alterations over the entire region coding for SEQ ID NO:2, wherein $n_n$ is the maximum number of nucleotide alterations, and is calculated by the formula $$n_n \leq x_n - (x_n \cdot y),$$

in which $x_n$ is the total number of nucleotides encoding for SEQ ID NO:2, and y has a value of 0.95, wherein any non-integer product of $x_n$ and y is rounded down to the nearest integer prior to subtracting such product from $x_n$; or
   (c) a nucleotide sequence which is at least 95% identical to SEQ ID NO:1 over the entire length of SEQ ID NO:1, which may include up to $n_n$ nucleotide alterations over the entire length of SEQ ID NO:1, wherein $n_n$ is the maximum number of nucleotide alterations, and is calculated by the formula $$n_n \leq x_n - (x_n \cdot y),$$

in which $x_n$ is the total number of nucleotides in SEQ ID NO:1, and y has a value of 0.95, wherein any non-integer product of $x_n$ and y is rounded down to the nearest integer prior to subtracting such product from $x_n$.

16. An isolated polynucleotide which is fully complementary to
 (a) a nucleotide sequence encoding the polypeptide of SEQ ID NO:2;
 (b) a nucleotide sequence comprising the polynucleotide sequence of SEQ ID NO:1; or
 (c) a nucleotide sequence consisting of the polynucleotide sequence of SEQ ID NO:1.

17. An isolated polynucleotide comprising a nucleotide sequence encoding a polypeptide that has at least 95% identity to the amino acid sequence of SEQ ID NO:6, over the entire length of SEQ ID NO:6, which may include up to $n_a$ amino acid alterations over the entire length of SEQ ID NO:6, wherein $x_a$ is the maximum number of amino acid alterations, and is calculated by the formula $$n_a \leq x_a - (x_a \cdot y),$$

in which $x_a$ is the total number of amino acids in SEQ ID NO:6, and y has a value of 0.95, wherein any non-integer product of $x_a$ and y is rounded down to the nearest integer prior to subtracting such product from $x_a$.

18. An isolated polynucleotide comprising a nucleotide sequence that has at least 95% identity over its entire length to a nucleotide sequence encoding the polypeptide of SEQ ID NO:6, which may include up to $n_n$ nucleotide alterations over the entire region coding for SEQ ID NO:6, wherein $n_n$ is the maximum number of nucleotide alterations, and is calculated by the formula $$n_n \leq x_n - (x_n \cdot y),$$

in which $x_n$ is the total number of nucleotides encoding for SEQ ID NO:6, and y has a value of 0.95, wherein any non-integer product of $x_n$ and y is rounded down to the nearest integer prior to subtracting such product from $x_n$.

19. An isolated polynucleotide comprising a nucleotide sequence which has at least 95% identity to that of SEQ ID NO:5 over the entire length of SEQ ID NO:5, which may include up to $n_n$ nucleotide alterations over the entire length of SEQ ID NO:5, wherein $n_n$ is the maximum number of nucleotide alterations, and is calculated by the formula $$n_n \leq x_n - (x_n \cdot y),$$

in which $x_n$ is the total number of nucleotides in SEQ ID NO:5, and y has a value of 0.95, wherein any non-integer product of $x_n$ and y is rounded down to the nearest integer prior to subtracting such product from $x_n$.

20. An isolated polynucleotide comprising a nucleotide sequence encoding the polypeptide of SEQ ID NO:6.

21. An isolated polynucleotide comprising the polynucleotide sequence set forth in SEQ ID NO:5.

22. The isolated polynucleotide of claim 21 consisting of the polynucleotide sequence of SEQ ID NO:1.

23. An isolated polynucleotide having at least 100 nucleotides in length obtainable by screening an appropriate library under stringent hybridization conditions with a labeled probe comprising the sequence of SEQ ID NO:5, said stringent hybridization conditions comprising overnight incubation of hybridization filters at 42° C. in a solution comprising 50% formamide, 5×SSC, 50 mM sodium phosphate having pH 7.6, 5× Denhardt's solution, 10% dextran sulfate, and 20 micrograms per ml denatured, sheared salmon sperm DNA, followed by washing the filters in 0.1×SSC at 65° C., wherein said polynucleotide encodes a metalloprotease polypeptide.

24. An isolated polynucleotide which is fully complementary to
 (a) a nucleotide sequence encoding a polypeptide that is at least 95% identical to the amino acid sequence of SEQ ID NO:6, over the entire length of SEQ ID NO:6, which may include up to $n_a$ amino acid alterations over the entire length of SEQ ID NO:6, wherein $n_a$ is the maximum number of amino acid alterations, and is calculated by the formula $$n_a \leq x_a - (x_a \cdot y),$$

in which $x_a$ is the total number of amino acids in SEQ ID NO:6, and y has a value of 0.95, wherein any non-integer product of $x_a$ and y is rounded down to the nearest integer prior to subtracting such product from $x_a$;
 (b) a nucleotide sequence that is at least 95% identical to a nucleotide sequence encoding the polypeptide of SEQ ID NO:6, over the entire region encoding for SEQ ID NO:6, which may include up to $n_n$ nucleotide alterations over the entire region coding for SEQ ID NO:6, wherein $n_n$ is the maximum number of nucleotide alterations, and is calculated by the formula $$n_n \leq x_n - (x_n \cdot y),$$

in which $x_n$ is the total number of nucleotides encoding for SEQ ID NO:6, and y has a value of 0.95, wherein any non-integer product of $x_n$ and y is rounded down to the nearest integer prior to subtracting such product from $x_n$; or
 (c) a nucleotide sequence which is at least 95% identical to SEQ ID NO:5 over the entire length of SEQ ID NO:5, which may include up to $n_n$ nucleotide alterations over the entire length of SEQ ID NO:5, wherein $n_n$ is the maximum number of nucleotide alterations, and is calculated by the formula $$n_n \leq x_n - (x_n \cdot y),$$

in which $x_n$ is the total number of nucleotides in SEQ ID NO:5, and y has a value of 0.95, wherein any non-integer product of $x_n$ and y is rounded down to the nearest integer prior to subtracting such product from $x_n$.

25. An isolated polynucleotide which is fully complementary to
 (d) a nucleotide sequence encoding the polypeptide of SEQ ID NO:6;
 (e) a nucleotide sequence comprising the polynucleotide sequence of SEQ ID NO:5; or
 (f) a nucleotide sequence consisting of the polynucleotide sequence of SEQ ID NO:5.

26. An isolated polypeptide comprising an amino acid sequence that has at least 95% identity to the amino acid sequence of SEQ ID NO:2, said identity being over the entire length of SEQ ID NO:2, which may include up to $n_a$ amino acid alterations over the entire length of SEQ ID NO:2, wherein $n_a$ is the maximum number of amino acid alterations, and is calculated by the formula $$n_a \leq x_a - (x_a \cdot y),$$

in which $x_a$ is the total number of amino acids in SEQ ID NO:2, and y has a value of 0.95, wherein any non-integer product of $x_a$ and y is rounded down to the nearest integer prior to subtracting such product from $x_a$.

27. The isolated polypeptide of claim 26 comprising the amino acid sequence of SEQ ID NO:2.

28. The isolated polypeptide of claim 27 consisting of the amino acid sequence of SEQ ID NO:2.

29. An isolated polypeptide comprising an amino acid sequence that has at least 95% identity to the amino acid sequence of SEQ ID NO:6, said identity being over the entire length of SEQ ID NO:6, which may include up to $n_a$ amino acid alterations over the entire length of SEQ ID NO:6, wherein $n_a$ is the maximum number of amino acid alterations, and is calculated by the formula $$n_a \leq x_a - (x_a \cdot y),$$

in which $x_a$ is the total number of amino acids in SEQ ID NO:6, and y has a value of 0.95, wherein any non-integer product of $x_a$ and y is rounded down to the nearest integer prior to subtracting such product from $x_a$.

30. The isolated polypeptide of claim 28 comprising the amino acid sequence of SEQ ID NO:6.

31. The isolated polypeptide of claim 30 consisting of the amino acid sequence of SEQ ID NO:6.

* * * * *